(12) United States Patent
Takahashi et al.

(10) Patent No.: US 10,874,596 B2
(45) Date of Patent: Dec. 29, 2020

(54) TOOTH WHITENING COMPOSITION

(71) Applicant: GC Corporation, Tokyo (JP)

(72) Inventors: Makoto Takahashi, Tokyo (JP); Manami Kurakazu, Tokyo (JP); Futoshi Fusejima, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 15/746,556

(22) PCT Filed: Jul. 13, 2016

(86) PCT No.: PCT/JP2016/070694
§ 371 (c)(1),
(2) Date: Jan. 22, 2018

(87) PCT Pub. No.: WO2017/022436
PCT Pub. Date: Feb. 9, 2017

(65) Prior Publication Data
US 2018/0214357 A1    Aug. 2, 2018

(30) Foreign Application Priority Data
Jul. 31, 2015   (JP) ................................. 2015-152829

(51) Int. Cl.
| A61K 8/22 | (2006.01) |
| A61K 8/24 | (2006.01) |
| A61Q 11/00 | (2006.01) |
| A61K 8/39 | (2006.01) |
| A61K 8/34 | (2006.01) |
| A61K 8/365 | (2006.01) |

(52) U.S. Cl.
CPC .................. *A61K 8/22* (2013.01); *A61K 8/24* (2013.01); *A61K 8/345* (2013.01); *A61K 8/365* (2013.01); *A61K 8/39* (2013.01); *A61Q 11/00* (2013.01)

(58) Field of Classification Search
CPC .................................. A61K 8/22; A61Q 11/00
USPC .......................................................... 424/53
See application file for complete search history.

(56) References Cited

U.S. PATENT DOCUMENTS

| 5,171,564 A | 12/1992 | Nathoo et al. |
| 5,683,679 A | 11/1997 | Sharma |
| 5,858,332 A | 1/1999 | Jensen et al. |
| 5,902,568 A * | 5/1999 | Ryles ........................ A61K 8/19 424/49 |
| 6,162,055 A * | 12/2000 | Montgomery ........... A61C 5/00 433/216 |
| 2003/0152528 A1 | 8/2003 | Singh et al. |
| 2003/0235549 A1 | 12/2003 | Singh et al. |
| 2004/0202621 A1 | 10/2004 | Orlowski et al. |
| 2005/0031552 A1 | 2/2005 | Mori et al. |
| 2006/0257822 A1 * | 11/2006 | Ghosh ................ A46B 15/0036 433/215 |
| 2006/0275225 A1 | 12/2006 | Prencipe et al. |
| 2007/0003494 A1 | 1/2007 | Mori et al. |
| 2009/0035231 A1 * | 2/2009 | Smigel ..................... A61K 8/22 424/53 |
| 2009/0275652 A1 | 11/2009 | Okano et al. |
| 2009/0311200 A1 | 12/2009 | Lambert et al. |
| 2014/0178443 A1 * | 6/2014 | Sagel ....................... A61K 8/42 424/401 |

FOREIGN PATENT DOCUMENTS

| JP | S56-095998 | 8/1981 |
| JP | S57-092095 | 6/1982 |
| JP | H5-194165 | 8/1993 |
| JP | 2001-508438 | 6/2001 |
| JP | 2002-502864 | 1/2002 |
| JP | 2005-060267 | 3/2005 |
| JP | 2006-516654 | 7/2006 |
| JP | 2006-528984 | 12/2006 |
| JP | 2007-008874 | 1/2007 |
| JP | 2008-120783 | 5/2008 |
| JP | 2009-161518 | 7/2009 |
| JP | 2011-526245 | 10/2011 |
| JP | 2012-180342 | 9/2012 |
| WO | 2002/000182 | 1/2002 |
| WO | 2003/099246 | 12/2003 |
| WO | 2007/090192 | 8/2007 |

OTHER PUBLICATIONS

International Search Report for PCT/JP2016/070694 dated Sep. 6, 2016.

* cited by examiner

*Primary Examiner* — Walter E Webb
(74) *Attorney, Agent, or Firm* — Ipusa, PLLC

(57) ABSTRACT

A tooth whitening composition includes a whitening component; a metal ion chelator; water; and polyalcohol, the weight ratio of the water and the polyalcohol being, water:polyalcohol=3.5:1 to 20:1, and also, the total amount of the water and the polyalcohol, in the composition, being greater than or equal to 50 wt. % and less than or equal to 85 wt. %.

1 Claim, No Drawings

TOOTH WHITENING COMPOSITION

BACKGROUND OF THE INVENTION

1. Field of the Invention

The present invention relates to a tooth whitening composition.

2. Description of the Related Art

Generally, whiteness of teeth is considered as an important factor from the standpoint of beauty, and demands for whitening teeth are increasing recently. For a method of whitening teeth, generally, a method of applying a composition including a whitening component to pigments (stains) on the teeth, and achromatizing or removing the pigments by the function of the component is known.

As the composition for whitening a tooth, for example, a composition consist of sodium magnesium silicate, urea peroxide, polyalcohol and a thickener swellable to the polyalcohol is known (see Patent Document 1, for example). However, as this composition does not include water, there is a problem that penetration of the whitening component to a surface of the tooth is weak and whitening capability is low.

On the other hand, when water is included in the composition, there is a problem of preservation stability such that the whitening component such as hydrogen peroxide or urea peroxide is decomposed while preserving it (when unused), and whitening capability of the composition is lowered.

In order to solve this problem of preservation stability, a paste material for tooth whitening is disclosed, consisting of a first paste component in which a powder hydrogen peroxide polyvinylpyrrolidone complex is mixed in a liquid component, and a second paste component in which a catalyst that activates hydrogen peroxide and a thickener are mixed in a liquid component (see Patent Document 2, for example). However, as the hydrogen peroxide polyvinylpyrrolidone complex is a complex, the generated amount of radicals is small compared with normal hydrogen peroxide, and there is a problem that sufficient whitening capability cannot be obtained after preserving it for long time.

Further, although the problem of preservation stability can be solved by using a binary system (two components), a mixing operation is necessary when using it, and there is a problem that the operation is complicated.

PATENT DOCUMENTS

[Patent Document 1] Japanese Laid-open Patent Publication No. 2005-60267
[Patent Document 2] Japanese Laid-open Patent Publication No. 2007-8874

SUMMARY OF THE INVENTION

The present invention is made in light of the above problems, and provides a tooth whitening composition of a one-paste system whose whitening capability is high and that has a good preservation stability.

The present inventors studied hard to solve the above described problems to complete the present invention by finding that a tooth whitening composition of a one-paste system whose whitening capability is high and that has a good preservation stability can be provided when the tooth whitening composition includes a whitening component, a metal ion chelator, water and polyalcohol, wherein the weight ratio of the water and the polyalcohol is within a specific range, and also, the total amount of the water and the polyalcohol is within a specific range.

In other words, the present invention relates to a tooth whitening composition including a whitening component; a metal ion chelator; water; and polyalcohol, the weight ratio of the water and the polyalcohol being, water:polyalcohol=3.5:1 to 20:1, and also, the total amount of the water and the polyalcohol, in the composition, being greater than or equal to 50 wt. % and less than or equal to 85 wt. %.

According to the tooth whitening composition of the invention, a tooth whitening composition of a one-paste system and including water whose whitening capability is high and quality degradation does not occur even when preserved for long time is provided.

DETAILED DESCRIPTION OF THE PREFERRED EMBODIMENTS

The tooth whitening composition of the embodiment is described in detail in the following.

The tooth whitening composition of the embodiment includes a whitening component (bleaching component), a metal ion chelator, water and polyalcohol, wherein the weight ratio of the water and the polyalcohol is water:polyalcohol=3.5:1 to 20:1, and also the total amount of the water and the polyalcohol, in the composition, is greater than or equal to 50 wt. % and less than or equal to 85 wt. %.

The whitening component included in the tooth whitening composition of the embodiment bleaches pigments (stains) on a surface of a tooth by achromatizing, removing the pigments or the like. Specifically, the whitening component is a material capable of generating a radical, and typically, peroxide. For example, hydrogen peroxide, urea peroxide, perborate, percarbonate, perphosphate, calcium peroxide, magnesium peroxide or the like may be exemplified. Further, a material such as chlorous acid, hypochlorous acid or the like that does not generate hydrogen peroxide may be used. Among them, hydrogen peroxide or urea peroxide is particularly preferable. Two or more of them may be used in combination at the same time. However, it is preferable not to mix peroxide in a form of a complex such as a hydrogen peroxide polyvinylpyrrolidone complex, as the generated amount of radicals is small compared with peroxide that is not in a form of a complex.

It is preferable that the mixed amount of the whitening component, in the tooth whitening composition, is greater than or equal to 1 wt. % and less than or equal to 30 wt. %. When the amount is greater than or equal to 1 wt. %, whitening force can be retained, and when the amount is less than or equal to 30 wt. %, preservation stability can be retained. More preferably, the mixed amount is greater than or equal to 3 wt. % and less than or equal to 25 wt. %.

The metal ion chelator included in the tooth whitening composition of the embodiment has a function to chemically capture metal ions such as platinum ions, ferrous ions or manganese ions that have a possibility to be mixed in the composition as trace impurities, and lower preservation stability of the composition by promoting decomposition of the whitening component, and has a function to improve the preservation stability of the composition. As the metal ion chelator, a condensed phosphoric acid or phosphate thereof is exemplified, and specifically, metaphosphoric acid, tripolyphosphoric acid, tetrapolyphosphoric acid, pyrophoric acid, hexametaphosphoric acid, sodium metaphosphate, sodium tripolyphosphate, sodium tetrapolyphosphate, sodium pyrophosphate, sodium orthophosphate, sodium hexametaphosphate, potassium metaphosphate, potassium tripolyphosphate, potassium tetrapolyphosphate, potassium pyrophosphate, potassium orthophosphate, potassium hexametaphosphate or the like is exemplified. As the metal ion chelator other than the condensed phosphoric acid, citric acid, glycine, ethylenediaminetetraacetic acid, succinic acid, adipic acid, a salt thereof or the like is exemplified. Two or more of them may be used in combination at the same time.

Among the exemplified metal ion chelators, the condensed phosphoric acid or phosphate thereof is particularly preferable as it has particularly good preservation stability when a large amount of water is included.

It is preferable that the mixed amount of the metal ion chelator, in the tooth whitening composition, is greater than or equal to 0.1 wt. % and less than or equal to 20 wt. %. When the amount is greater than or equal to 0.1 wt. %, preservation stability of the whitening component can be retained, and when the amount is less than or equal to 20 wt. %, whitening force can be retained. More preferably, the mixed amount is greater than or equal to 0.5 wt. % and less than or equal to 10 wt. %.

The tooth whitening composition of the embodiment includes water and polyalcohol as solvent, wherein the weight ratio is water:polyalcohol=3.5:1 to 20:1, and also, the total amount of the water and the polyalcohol, in the composition, is greater than or equal to 50 wt. % and less than or equal to 85 wt. %. When the amounts of the water and the polyalcohol are within the above range, the tooth whitening composition of a one-paste system whose whitening capability is high and quality degradation does not occur even when preserved for long time is provided.

The polyalcohol means an alcohol that contains two or more hydroxyl groups in one molecule. As the polyalcohol, for example, glycerin, diglycerol, polyglycerol, propylene glycol, dipropylene glycol, polypropylene glycol, ethylene glycol, diethylene glycol, polyethylene glycol, polyethylene glycol monomethyl ether, 1,2-pentanediol, 1,2-hexanediol, 1,2-octanediol, sorbitol, mannitol or the like is exemplified. Two or more of them may be used in combination at the same time.

The weight ratio of the water and the polyalcohol mixed in the composition is, water:polyalcohol=3.5:1 to 20:1. When the ratio of the water to be greater than or equal to water:polyalcohol=3.5:1, whitening force can be retained, and when the ratio of the water to be less than or equal to water:polyalcohol=20:1, preservation stability can be retained. More preferably, the amount is, water:polyalcohol=5:1 to 8:1.

The total amount of the water and the polyalcohol mixed in the composition, in the composition, is greater than or equal to 50 wt. % and less than or equal to 85 wt. %. When the total amount is greater than or equal to 50 wt. %, whitening force can be retained, and when the total amount is less than or equal to 85 wt. %, preservation stability can be retained. More preferably, the total amount is greater than or equal to 55 wt. % and less than or equal to 80 wt. %.

In addition to the above described conditions, it is preferable that the mixed amount of the water, in the composition, is greater than or equal to 50 wt. % and less than or equal to 75 wt. % as whitening force is furthermore increased. More preferably, the mixed amount is greater than or equal to 55 wt. % and less than or equal to 70 wt. %.

The tooth whitening composition of the embodiment may include a solvent other than water and polyalcohol. As the solvent other than water and polyalcohol, for example, monohydroxy alcohol such as methanol, ethanol, 1-propanol, 2-propanol or 2-methyl-2-propanol, acetone, hexane, benzene, toluene or the like is exemplified. However, it is preferable that the amount of the solvent other than water and polyalcohol, in the composition, is less than or equal to 10 wt. % because if the mixed amount of the solvent other than water and polyalcohol is large, whitening force may be lowered. More preferably, the mixed amount is less than or equal to 5 wt. %.

The tooth whitening composition of the embodiment may further include a thickener. By including the thickener, viscosity is provided to the tooth whitening composition, and operativity can be improved. As the thickener, for example, an organic thickener such as sodium carboxymethyl cellose, sodium alginate, carboxymethyl cellulose, sodium carboxymethyl cellulose, calcium carboxymethyl cellulose, carboxypolymethylene, methyl vinyl ether/maleic anhydride copolymer, dimethyl polysiloxane, sodium starch glycolate, sodium starch phosphate ester, sodium polyacrylate, methyl cellulose, crystalline cellulose, hydroxyethyl cellulose, hydroxymethyl cellulose, hydroxypropyl cellulose or polyvinylpyrrolidone, an inorganic thickener such as sodium magnesium silicate, lithium magnesium sodium silicate, acrylic acid/behenic acid copolymer, calcium carbonate, calcium silicate, magnesium silicate, silica powders, various glasses, amorphous hydrated silicic acid or fumed silica, carboxyvinyl polymer or the like may be exemplified. Two or more of them may be used in combination at the same time.

When the thickener is mixed, it is preferable that the mixed amount, in the composition, is greater than or equal to 0.5 wt. % and less than or equal to 30 wt. %. When the mixed amount is greater than or equal to 0.5 wt. %, a sufficient effect of increasing the viscosity of the tooth whitening composition can be obtained so that the composition can stay at the surface of the tooth, for example, and when the mixed amount is less than or equal to 30 wt. %, appropriate viscosity can be obtained. More preferably, the mixed amount is greater than or equal to 1 wt. % less than or equal to 25 wt. %.

The tooth whitening composition of the embodiment may further include a colorant. By mixing the colorant, visibility of the composition is improved. As the colorant, titanium oxide, silicon dioxide, zinc oxide, aluminum oxide, magnesium oxide, zirconium oxide or the like is exemplified. Two or more of them may be used in combination at the same time.

When the colorant is mixed in the tooth whitening composition, it is preferable that the mixed amount of the colorant is greater than or equal to 0.01 wt. % and less than or equal to 5 wt. %. When the mixed amount is greater than or equal to 0.01 wt. %, a sufficient coloring effect for the paste can be obtained, and when the mixed amount is less than or equal to 5 wt. %, preservation stability can be retained.

It is preferable that the pH of the tooth whitening composition of the embodiment is adjusted to be greater than or equal to 5.5 and less than or equal to 9.5. When the pH is greater than or equal to 5.5, decalcification of the tooth can be prevented, and when the pH is less than or equal to 9.5, preservation stability of the tooth whitening composition can be retained.

The tooth whitening composition of the embodiment may further include a pH adjustor for adjusting the pH of the tooth whitening composition. As the pH adjustor, disodium phosphate, potassium hydroxide, sodium hydroxide, ammonium hydroxide, sodium carbonate, monoethanolamine, diethanolamine, triethanolamine or the like is exemplified. Two or more of them may be used in combination at the same time.

When the pH adjustor is mixed in the tooth whitening composition, it is preferable that the mixed amount of the pH adjustor is greater than or equal to 0.1 wt. % and less than or equal to 25 wt. %. When the mixed amount is greater than or equal to 0.1 wt. %, a sufficient pH adjusting effect can be obtained, and when the mixed amount is less than or equal to 25 wt. %, preservation stability can be retained.

The tooth whitening composition of the embodiment may further include a perfume, a pigment, a stabilizer, a solvent or the like in addition to the above described components.

EXAMPLES

Hereinafter, the present embodiment is described more in detail by examples (E1 to E10) and comparative examples (C1 to C10). However, the present invention is not limited to these examples.

Source material components were kneaded by compositions illustrated in Table 1 and Table 2, and tooth whitening compositions of paste were prepared. The following tests were conducted using these compositions, and evaluated the tooth whitening composition of the embodiment. Here, the unit of the values in Table 1 and Table 2 is wt. %.

(Whitening Component Releasing Amount)

0.02 g of each of the prepared tooth whitening compositions was coated on a transparent sheet (material: polyethylene terephthalate) of 20 mm×20 mm×0.1 mm, and the respective tooth whitening composition was sandwiched by a similar transparent sheet such that the total thickness (two transparent sheets+each tooth whitening composition) became 0.5 mm. This was calmly put in 30 mL of distilled water in a glass container and was immersed. This was stood at 37° C. for 2 hours, and 25 mL of supernatant liquid was calmly sampled. A redox titration was conducted for the supernatant liquid in accordance with a "test method of hydrogen peroxide concentration" of JIS T 6542:2013 "materials for external tooth bleaching". At this time, as the concentration is low compared with a normal titration for measuring concentration, the titration was conducted using 0.01M sodium thiosulfate solution. The obtained amount of hydrogen peroxide was converted by multiplying by 1.2, and the "hydrogen peroxide amount released in 30 mL of distilled water" was calculated. Separately, the "hydrogen peroxide amount included in 0.02 g of the tooth whitening composition" was obtained by a redox titration in accordance with a "test method of hydrogen peroxide concentration" of JIS T 6542:2013 "materials for external tooth bleaching".

Whitening component releasing rate (%) (hydrogen peroxide amount released in 30 mL of distilled water)/(hydrogen peroxide amount included in 0.02 g of the tooth whitening composition)×100

Here, in a viewpoint of whitening capability, it is preferable that the whitening component releasing rate is greater than or equal to 30%.

(Tooth Whitening Test)

After cutting a root portion of an extracted front tooth of a cow, a dental pulp was removed to be used as a test piece of a whitening test. First, color (CIE $L^*a^*b^*$ value) of a surface of the test piece was measured. Next, after coating each of the prepared tooth whitening compositions, the test piece was preserved under an environment of temperature 37° C. and relative humidity 100% for 2 hours, and water washed. After repeating a series of operations from the coating to water washing for 14 times in total, color (CIE $L^*a^*b^*$ value) of the surface of the test piece was measured. The color difference $\Delta Eab^* (=\sqrt{(\Delta L)^2+(\Delta a)^2+(\Delta b)^2})$ between before and after the whitening test was calculated, and this was used as color change by whitening. Here, as the larger the color difference $\Delta Eab^*$ is, the higher the whitening capability is, color change by whitening was evaluated by the following indexes. The color change by whitening was evaluated by the following indexes. The evaluated results are illustrated in Table 1 and Table 2.

AA: when $\Delta Eab^*$ is greater than or equal to 8

A: when $\Delta Eab^*$ is greater than or equal to 4 and less than 8

B: when $\Delta Eab^*$ is less than 4

(Preservation Test)

After filling each of the prepared tooth whitening compositions in a syringe, the syringe was stood at 23° C. A redox titration was conducted in accordance with a "test method of hydrogen peroxide concentration" of JIS T 6542:2013 "materials for external tooth bleaching" on each of a first day and predetermined date. Then, days necessary for hydrogen peroxide concentration to be less than 70% of initial concentration were obtained.

Here, from a viewpoint of preservation stability, it is preferable that the above days are greater than or equal to 350 days.

(pH Measurement)

1 g of each of the prepared tooth whitening compositions was completely dissolved in 19 g of distilled water, and pH was measured by a pH measuring device.

TABLE 1

|  |  | E1 | E2 | E3 | E4 | E5 | E6 | E7 | E8 | E9 | E10 |
|---|---|---|---|---|---|---|---|---|---|---|---|
|  | WATER | 60.3 | 41 | 60.3 | 77 | 80 | 55.3 | 42 | 60 | 47.6 | 55.6 |
| POLYALCOHOL | POLYETHYLENE GLYCOL | 14.5 | 11 |  | 2 | 4.8 | 8 | 3.3 | 2 | 2 |  |
|  | PROPYLENE GLYCOL |  |  |  | 2 |  |  | 3.3 | 2 |  | 4.6 |
|  | GLYCERIN |  |  | 10.5 |  |  | 7.5 | 3.3 | 2 | 3.5 |  |
| pH ADJUSTOR | SODIUM HYDROXIDE |  | 4 | 3 | 1 |  | 3 | 5 |  | 3 |  |
|  | POTASSIUM HYDROXIDE | 0.1 |  | 2 |  | 2 |  | 3 | 0.4 | 0.9 | 0.3 |
| WHITENING COMPONENT | HYDROGEN PEROXIDE | 10 | 3 | 5 | 2 | 2 |  | 3 |  |  |  |
|  | UREA PEROXIDE |  | 10 | 5 |  |  | 10 | 10 | 15 | 20 | 18 |
| THICKENER | POLYVINYLPYRROLIDONE |  | 5 |  |  |  | 3 | 7 | 7 | 5 | 5 |
|  | CARBOXYPOLYMETHYLENE |  | 5 | 5 |  |  |  | 10 | 3 |  | 5 |
|  | METHYL VINYL ETHER/ MALEIC ANHYDRIDE COPOLYMER | 7 |  | 2 | 10 | 5 | 4 |  |  | 5 |  |
| METAL ION CHELATOR | SODIUM PYROPHOSPHATE | 2 |  |  | 3 |  |  |  | 8 |  |  |
|  | SODIUM TRIPOLYPHOSPHATE | 5 | 10 | 3 | 3 |  | 3 |  |  |  |  |
|  | SODIUM METAPHOSPHATE |  | 5 |  |  | 6 | 5 | 3 |  |  | 5 |

TABLE 1-continued

|  |  | E1 | E2 | E3 | E4 | E5 | E6 | E7 | E8 | E9 | E10 |
|---|---|---|---|---|---|---|---|---|---|---|---|
|  | SODIUM HEXAMETAPHOSPHATE |  | 5 | 4 |  |  |  | 3 |  |  | 5 |
|  | CITRIC ACID |  |  |  |  |  |  | 3 |  | 10 |  |
| COLORANT | TITANIUM DIOXIDE | 0.1 |  | 0.1 |  | 0.1 | 0.1 |  | 0.1 |  |  |
|  | ZINC OXIDE |  | 1 |  |  |  | 0.1 | 1 |  | 1 | 1 |
| OTHER ADDITIVES | PERFUME | 1 |  | 0.1 |  | 0.1 | 1 | 0.1 | 0.5 | 2 | 0.5 |
|  | TOTAL | 100 | 100 | 100 | 100 | 100 | 100 | 100 | 100 | 100 | 100 |
|  | WATER/ALCOHOL RATIO | 4.2 | 3.7 | 5.7 | 19.3 | 16.7 | 3.6 | 4.2 | 10.0 | 8.7 | 12.1 |
|  | TOTAL AMOUNT OF WATER AND ALCOHOL | 74.8 | 52.0 | 70.8 | 81.0 | 84.8 | 70.8 | 51.9 | 66.0 | 53.1 | 60.2 |
| TEST RESULTS | WHITENING COMPONENT RELEASING AMOUNT (%) | 35 | 32 | 41 | 61 | 53 | 34 | 30 | 48 | 44 | 50 |
|  | WHITENING TEST | A | A | AA | AA | AA | A | A | AA | AA | AA |
|  | PRESERVATION TEST (DAYS) | 670 | 700 | 530 | 390 | 380 | 710 | 680 | 460 | 500 | 450 |
|  | pH | 9 | 5.9 | 6.2 | 7.1 | 6.7 | 9.4 | 6.8 | 7.5 | 5.6 | 8.6 |

TABLE 2

|  |  | C1 | C2 | C3 | C4 | C5 | C6 | C7 | C8 | C9 | C10 |
|---|---|---|---|---|---|---|---|---|---|---|---|
|  | WATER | 48.5 | 55 | 61.4 | 55 | 76.8 | 40 |  | 55 | 50 | 68 |
| POLYALCOHOL | POLYETHYLENE GLYCOL |  |  |  | 8.3 |  |  | 8 | 8 |  | 3.2 |
|  | PROPYLENE GLYCOL | 15 |  | 4 |  |  | 5 | 30 |  | 20 |  |
|  | GLYCERIN | 15 | 34.9 | 15 | 8 |  |  | 30 | 11 |  |  |
| pH ADJUSTOR | SODIUM HYDROXIDE |  | 2 | 2 | 5 | 2 |  | 2 | 2 | 0.4 | 0.8 |
|  | POTASSIUM HYDROXIDE | 0.5 | 1 | 0.1 | 0.2 | 0.1 | 7 |  | 1 | 3 |  |
| WHITENING COMPONENT | HYDROGEN PEROXIDE | 5 |  |  | 3 |  |  |  | 3 | 3 |  |
|  | UREA PEROXIDE | 5 |  | 7 |  | 10 | 10 | 10 |  | 3 | 10 |
| THICKENER | POLYVINYLPYRROLIDONE |  | 4 |  | 10 | 5 | 5 | 2 |  | 2 |  |
|  | CARBOXYPOLYMETHYLENE | 3 | 3 | 7 |  | 5 | 10 | 8 | 5 |  |  |
|  | METHYL VINYL ETHER/ MALEIC ANHYDRIDE COPOLYMER | 7 |  | 3 |  |  |  |  | 5 | 8 | 10 |
| METAL ION CHELATOR | SODIUM PYROPHOSPHATE |  |  |  |  |  | 3 | 3 |  | 5 |  |
|  | SODIUM TRIPOLYPHOSPHATE |  |  |  | 10 |  |  |  |  |  | 2 |
|  | SODIUM METAPHOSPHATE |  |  |  |  |  | 5 |  | 10 | 5 | 5 |
|  | SODIUM HEXAMETAPHOSPHATE |  |  |  |  |  | 5 | 5 |  |  |  |
|  | CITRIC ACID |  |  |  |  |  | 8 |  |  |  |  |
| COLORANT | TITANIUM DIOXIDE |  | 0.1 |  |  | 0.1 | 1 | 1 |  | 0.1 |  |
|  | ZINC OXIDE |  |  |  |  |  |  |  | 0.5 | 0.5 | 0.5 |
| OTHER ADDITIVES | PERFUME | 1 |  | 0.5 | 0.5 | 1 | 1 | 0.5 |  |  | 0.5 |
|  | TOTAL | 100 | 100 | 100 | 100 | 100 | 100 | 100 | 100 | 100 | 100 |
|  | WATER/ALCOHOL RATIO | 1.6 | 1.6 | 3.2 | 3.4 | — | 8.0 | 0 | 2.9 | 2.5 | 21.3 |
|  | TOTAL AMOUNT OF WATER AND ALCOHOL | 78.5 | 89.9 | 80.4 | 71.3 | 76.8 | 45.0 | 68 | 74.0 | 70.0 | 71.2 |
| TEST RESULTS | WHITENING COMPONENT RELEASING AMOUNT (%) | 12 | 12 | 30 | 21 | 65 | 23 | 7 | 18 | 17 | 62 |
|  | WHITENING TEST | B | B | A | B | AA | B | B | B | B | AA |
|  | PRESERVATION TEST (DAYS) | 200 | 180 | 140 | 690 | 80 | 540 | 800 | 780 | 720 | 130 |
|  | pH | 8 | 7 | 7.2 | 7.3 | 5.9 | 6.1 | 7.2 | 6.8 | 6.9 | 5.6 |

As illustrated in Table 1, for all of the examples (E1 to E10) each satisfying the condition that the weight ratio of the water and the polyalcohol is, water:polyalcohol=3.5:1 to 20:1, and also, the total amount of the water and the polyalcohol, in the composition, is greater than or equal to 50 wt. % and less than or equal to 85 wt. %, the whitening component releasing rate was greater than or equal to 30%, and the evaluation result of the tooth whitening test was as good as "AA" or "A". Further, for all of the examples (E1 to E10), days necessary for hydrogen peroxide concentration to be less than 70% of the initial concentration in the preservation test were greater than or equal to 350 days.

On the other hand, as illustrated in Table 2, for the comparative examples (C1 to 010) each not satisfying both of or one of the above described conditions of the weight ratio of water and polyalcohol, and the total amount of the water and the polyalcohol, it was difficult to satisfy both of the whitening capability and the preservation stability.

Although a preferred embodiments and examples have been specifically illustrated and described, the present invention is not limited to the above described embodiments and examples, and it is to be understood that minor modifications may be made therein without departing from the spirit and scope of the invention as defined by the claims.

The present application is based on and claims the benefit of priority of Japanese Priority Application No. 2015-152829 filed on Jul. 31, 2015, the entire contents of which are hereby incorporated by reference.

What is claimed is:

1. A tooth whitening composition comprising:
   a whitening component that contains hydrogen peroxide and/or urea peroxide;

a metal ion chelator that is one or more of sodium pyrophosphate, sodium tripolyphosphate, sodium metaphosphate, sodium hexametaphosphate, and citric acid;
water; and
polyalcohol,
the weight ratio of the water and the polyalcohol being, water : polyalcohol=3.6:1 to 19.3:1, and also, the total amount of the water and the polyalcohol, in the composition, being greater than or equal to 51.9 wt. % and less than or equal to 85 wt. %,
the amount of the hydrogen peroxide and/or urea peroxide in the composition being greater than or equal to 2 wt. % and less than or equal to 20 wt. %,
the amount of the metal ion chelator in the composition being greater than or equal to 6 wt. % and less than or equal to 20 wt. %,
the polyalcohol being one or more kinds of polyethylene glycol, propylene glycol, and glycerin.

* * * * *